United States Patent [19]

Mase et al.

[11] Patent Number: 4,541,900
[45] Date of Patent: Sep. 17, 1985

[54] METHOD FOR HEATING SOLID ELECTROLYTE

[75] Inventors: Syunzo Mase, Aichi; Shigeo Soejima, Nagoya, both of Japan

[73] Assignee: NGK Insulators, Ltd., Japan

[21] Appl. No.: 447,174

[22] Filed: Dec. 6, 1982

[30] Foreign Application Priority Data

Oct. 8, 1982 [JP] Japan ................. 57-177047

[51] Int. Cl.$^4$ .................. G01N 27/46; H05B 3/10
[52] U.S. Cl. .................... 204/1 T; 204/424; 204/425; 204/426; 204/427; 219/200; 219/553; 338/7
[58] Field of Search ......... 219/270, 553, 200, 552; 204/421–429, 1 S; 338/330, 22 R, 22 SD, 7.9

[56] References Cited

U.S. PATENT DOCUMENTS

| | | | |
|---|---|---|---|
| 3,654,112 | 4/1972 | Beekmans et al. | 204/1 S |
| 4,129,491 | 12/1978 | Obiaya | 204/428 |
| 4,157,948 | 6/1979 | Maurer | 204/426 |
| 4,300,990 | 11/1981 | Maurer | 204/425 |
| 4,407,704 | 10/1983 | Mase et al. | 204/1 S |

FOREIGN PATENT DOCUMENTS

| | | | |
|---|---|---|---|
| 0030164 | 6/1981 | European Pat. Off. | 204/427 |
| 56-79246 | 6/1981 | Japan | 204/428 |

*Primary Examiner*—T. Tung
*Attorney, Agent, or Firm*—Parkhurst & Oliff

[57] ABSTRACT

The disclosed heater with solid electrolyte has a resistor embedded in or tightly secured to a solid electrolyte and an AC power source connected to the resistor, so that heat is generated both in the resistor by an alternating current from the AC power source and in the solid electrolyte by an alternating current flowing therethrough depending on the temperature-sensitive resistance of the solid electrolyte being heated by the resistor.

6 Claims, 7 Drawing Figures

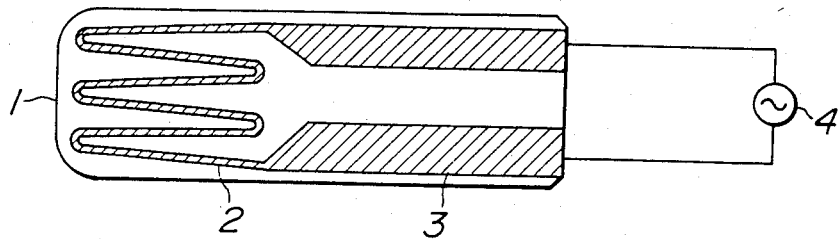
FIG_1
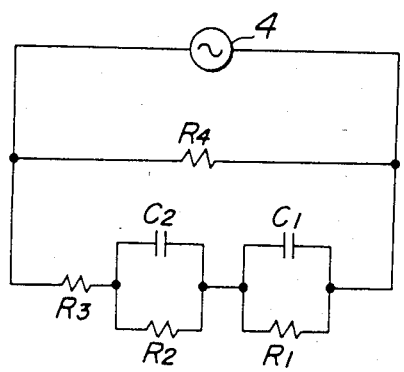
FIG_2
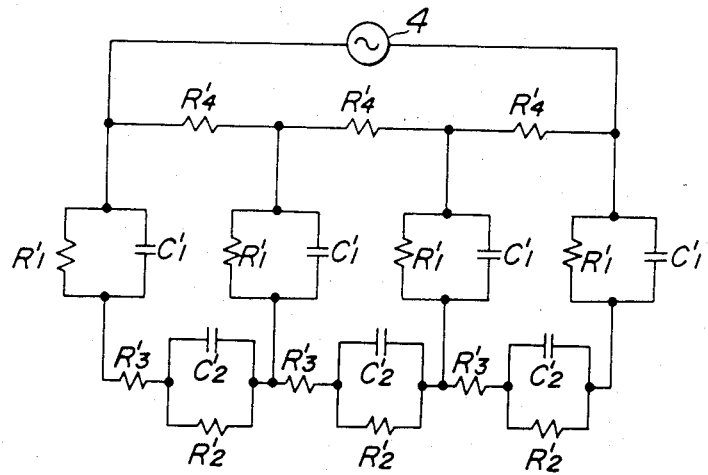
FIG_3

FIG_6
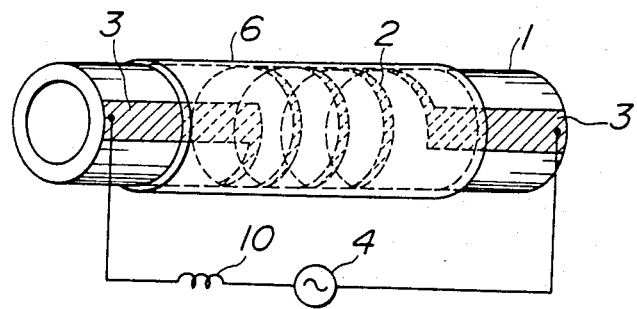
FIG_7
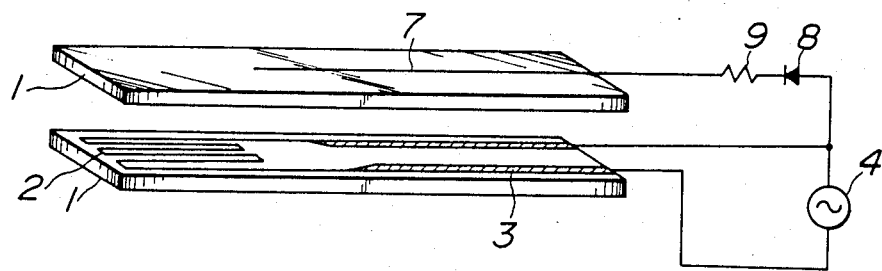

METHOD FOR HEATING SOLID ELECTROLYTE

BACKGROUND OF THE INVENTION

1. Field of the Invention

This invention relates to a heater with solid electrolyte, and more particularly to a ceramic heater having an excellent durability at high temperatures.

2. Description of the Prior Art

A ceramic heater comprising an electric resistor gastightly sealed in a ceramic insulator, such as a tungsten wire gastightly sealed in an alumina ceramics, has been known.

The ceramic heater of the prior art has a shortcoming in that the practicable highest temperature at which the ceramic heater can be used is limited to a comparatively low level of about 800° C. at most, because when the temperature of ceramics forming the insulator thereof is raised, the insulation of the ceramics is reduced and oxygen diffusion tends to occur through the ceramics.

SUMMARY OF THE INVENTION

Therefore, an object of the present invention is to obviate the above-mentioned shortcoming of the prior art by providing an improved heater with solid electrolyte.

Another object of the invention is to provide a ceramic heater of simple construction having an excellent durability at a high temperature.

An embodiment of the heater with solid electrolyte according to the present invention comprises a solid electrolyte, preferably an oxygen-ion-conductive solid electrolyte, an electric resistor embedded in or tightly secured to surface of the solid electrolyte, and an AC power source connected to opposite ends of the electric resistor so as to flow an alternating current to the resistor, whereby heat is generated both in the electric resistor by flowing the alternating current and in the solid electrolyte by flowing an alternating current therethrough depending on the temperature-sensitive resistance of the solid electrolyte being heated by the electric resistor.

In operation of the heater according to the present invention, when an alternating current, preferably an alternating current at a frequency higher than a certain value, is applied to the resistor in tight contact with the solid electrolyte, then the solid electrolyte is heated by the Joule heat generated in the resistor, and as the temperature of the solid electrolyte rises the resistance value of the solid electrolyte is reduced to allow the alternating current to flow into the solid electrolyte for generating heat within the solid electrolyte. Besides, the heater of the invention endures very high temperatures for a long time of use.

BRIEF DESCRIPTION OF THE DRAWINGS

For a better understanding of the invention, reference is made to the accompanying drawings, in which:

FIG. 1 is a schematic sectional view of a heater with electrolyte which is an embodiment of the present invention;

FIGS. 2 and 3 are electric equivalent circuit diagrams of a heater with electrolyte according to the present invention;

FIG. 6 is a perspective view of another embodiment of the invention which uses a tubular solid electrolyte; and FIG. 7 is an exploded perspective view of another heater with electrolyte according to the present invention, showing the mechanical construction and electric connection thereof.

Figure 4:
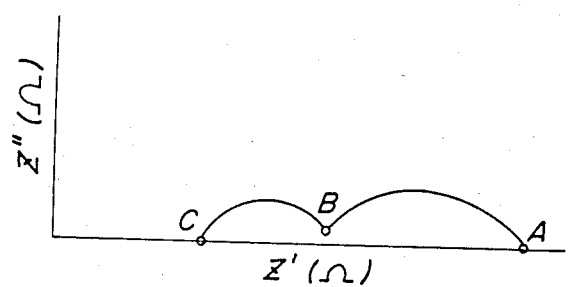
FIG. 4 is a graph showing the complex impedance characteristics of a heater with electrolyte according to the present invention.

Throughout different views of the drawings, 1 is a solid electrolyte, 2 is an electric resistor, 3 is a terminal, 4 is an AC power source, 5 is a throughhole, 6 is a gastight layer, 7 is an auxiliary electrode, 8 is a diode, 9 is another electric resistor, and 10 is an inductor.

DESCRIPTION OF THE PREFERRED EMBODIMENTS

Referring to FIG. 1 showing a heater with solid electrolyte as an embodiment of the present invention, a solid electrolyte 1 is made of zirconia ceramics containing yttria added therein. An electric resistor 2 made of platinum or the like is disposed on surface of the solid electrolyte 1 in tight contact therewith, and terminals 3 are connected to opposite ends of the resistor 2, so that an AC power source 4 is connected to the terminals 3.

When the output voltage of the AC power source 4 is applied to the electric resistor 2 through the terminals 3, an alternating current flows through the resistor 2 and generates Joule heat in the resistor 2, and the Joule heat thus generated heats the solid electrolyte 1 in tight contact with the resistor 2. As the temperature of the solid electrolyte 1 rises to a certain level, it becomes oxygen-ion-conductive and its electric resistance is reduced. Accordingly, a part of the electric current flowed to the resistor 2 flows into the solid electrolyte 1, and the solid electrolyte 1 itself is heated by the alternating current flowing therethrough.

It is noted that an alternating current can flow through and cause heat generation in the solid electrolyte 1 without any adverse effects to the properties of the solid electrolyte 1, provided that the magnitude of the alternating current flowing through the solid electrolyte 1 is such that polarization characteristics in the positive half cycle and the negative half cycle of the alternating current flowing through the solid electrolyte 1 are symmetrical relative to the zero point of the alternating current, so that the alternating current does not cause any substantial chemical reactions at the interface between the resistor 2 and the solid electrolyte 1.

The behavior of the alternating current flowed to the resistor 2 will be described now in detail.

FIG. 2 shows an electric equivalent circuit diagram of a heat generating portion consisting of the resistor 2 and the solid electrolyte 1. In the figure, $C_1$ is an electrostatic capacitance component due to the polarization at the interface between the resistor 2 and the solid electrolyte 1, $R_1$ is a polarization resistance component due to the interface between the resistor 2 and the solid electrolyte 1, $C_2$ is an electrostatic capacitance component due to the grain boundaries of the solid electrolyte 1, $R_2$ is a resistance component due to the grain boundaries of the solid electrolyte 1, $R_3$ is a resistance component representing resistances of the crystal grains of the solid electrolyte 1, and $R_4$ is the resistance of the resistor 2.

In reality, the constants of the equivalent circuit of FIG. 2 are divided into a large number of similarly defined constants $C_1'$, $R_1'$, $C_2'$, $R_2'$, and $R_3'$ relating to individual crystal grains constituting the solid electrolyte 1, and such divided constants are connected to resistances $R_4'$ of constituent sections of the resistor 2 in a more complicated manner as shown in FIG. 3.

The frequency characteristics of the equivalent circuit of FIG. 2 can be expressed by a complex impedance formula $Z=Z'-jZ''$ which can be plotted as a curve including two continuous arcuate potions as shown in FIG. 4. In the figure, the resistance value of the point A corresponds to the quantity of $R_4(R_1+R_2+R_3)/(R_1+R_2+R_3+R_4)$, the resistance value of the point B corresponds to the quantity of $R_4(R_2+R_3)/(R_2+R_3+R_4)$, and the resistance value of the point C corresponds to the quantity of $R_3 \cdot R_4/(R_3+R_4)$. The polarization from the point A to the point B on the frequency characteristics curve of FIG. 4 is mainly due to the resistance components $R_1$, $R_2$, $R_3$, and $R_4$ and the capacitance components $C_1$ and $C_2$, while that from the point B to the point C is mainly due to the resistance components $R_2$, $R_3$, and $R_4$ and the capacitance component $C_2$. As regards the variation of the complex impedance characteristics with the frequency variation, the point A represents DC, and as the frequency increases, the complex impedance varies along the arcuate locus toward the point B and further along the arcuate locus toward the point C.

When a direct current or an alternating current with a low frequency in the neighborhood of the point A of FIG. 4 is applied to the resistor 2, most of the current flows through the resistance components $R_4$ and $R_1$, and only little of it flows through the capacitance component $C_1$. The polarization due to the resistance component $R_1$ is usually non-linear and has poor symmetry. If this polarization is too large, decomposition of the solid electrolyte and the peeling of the resistor can be caused, and the durability of the heater with solid electrolyte is deteriorated.

When an electric current with a frequency in the neighborhood of the point B or higher than that of the point B is applied to the resistor 2, the interface impedance between the resistor 2 to which the alternating current is flowed and the solid electrolyte 1 becomes largely independent of the interface capacitance between the resistor 2 to which the alternating current is flowed and the solid electrolyte 1, and the alternating current flows mainly through the resistance component $R_4$ and the capacitance component $C_1$, and only little of it flows through the resistance component $R_1$. More particularly, in this case, the polarization due to the alternating current through the solid electrolyte mainly consists of the polarization in the inside of the solid electrolyte, so that the alternating current hardly contributes to electrode reactions and excellent durability of the heater with solid electrolyte can be ensured.

The frequency for the point B of FIG. 4 varies depending on the kind, microstructure, temperature, and shape of the solid electrolyte 1 used. For instance, in the case of a 1 mm thick zirconia ceramics electrolyte having a chemical composition of $(ZrO_2)_{0.94}(Y_2O_3)_{0.06}$ and containing 1 weight % of clay which electrolyte had the resistor mounted thereon as shown in FIG. 1, the frequency for the point B was 50 Hz at 350° C. and 3 kHz at 600° C.

Examples of the solid electrolyte to be used in the heater with solid electrolyte according to the present invention are the above-mentioned zirconia ceramics, thoria ($ThO_2$), β-alumina, aluminum nitride, NASICON, $SrCeO_3$, solid solutions of $Bi_2O_3$-(oxides of rare earth element) system, $La_{1-x}Ca_xYO_{3-\alpha}$, and the like. As to the material of the resistor, metals such as tungsten, molybdenum, nickel, iridium, rhodium, platinum, gold, silver, palladium, ruthenium, and the like, or alloys thereof are preferable because of their high durability, but compounds such as zinc oxide, $LaCrO_3$, $LaB_6$, SiC, and the like can be also used.

In order to securely mount the resistor to the solid electrolyte, a variety of methods are available; for instance, vacuum evaporation, sputtering, electroless plating, pyrolysis or reduction of a solution of metallic salt, baking of paste, cermet or flame spray, or the other known methods for mounting electrodes to ceramics or the like. To prevent the evaporation and contamination of the resistor during operation, the resistor can be protected by a refractory coating or by embedding the resistor in the solid electrolyte. Preferably, fine powder of zirconia, alumina, or the like is mixed in the material of the resistor, so as to prevent the resistor from being peeled off or broken due to firing during operation and to regulate the resistance value of the resistor.

In the heater with solid electrolyte according to the present invention, it is possible to accurately measure the temperature of the heater with excellent response to temperature change by measuring the impedance as seen from the opposite ends of the resistor, which impedance is a composite of the temperature-sensitive resistance of the resistor alone and the temperature-sensitive impedance of the solid electrolyte.

The construction of the heater with solid electrolyte according to the present invention is not restricted to that of FIG. 1. For instance, in the embodiment of FIG. 5, a solid electrolyte 1 has two resistors 2 and 2' secured to opposite surfaces thereof, and the two resistors 2 and 2' are electrically connected in series by a conductor in a throughhole 5 bored across the thickness of the solid electrolyte 1. A porous gastight layer 6 is disposed on that surface of the solid electrolyte 1 which carries one of the two resistors, e.g., the resistor 2' in the illustrated embodiment, and an AC power source 4 is connected across the serial resistors 2 and 2' through an inductor 10.

Referring to FIG. 6, a tubular solid electrolyte 1 can be used, and a spiral resistor 2 can be mounted on the outer surface of the tubular electrolyte 1. Terminals 3 are connected to opposite ends of the resistor 2, and the outer surface of the tubular solid electrolyte 1 carrying the resistor 2 is covered by a gastight layer 6 having the same chemical composition as that of the solid electrolyte 1. An AC power source 4 is connected to the terminals 3 through an inductor 10 in this embodiment.

When a resistor 2 used is made of a metal which is susceptible to oxidation at high temperatures, such as tungsten or molybdenum, it is preferable to airtightly seal the resistor 2 in the inside of a solid electrolyte 1 while forming an auxiliary electrode 7 on the surface of the solid electrolyte 1 as shown in FIG. 7. The output from an AC power source 4 is rectified by a diode 8 in series with another resistor 9, and the thus rectified DC voltage is applied across the auxiliary electrode 7 and the resistor 2, so as to cause the resistor 2 to act as a cathode for preventing the oxidation thereof.

If an AC power source 4 producing rectangular waves or pulses is used, it is preferable to insert an inductor 10 between the AC power source 4 and the resistor 2 in series therewith, so as to prevent induction noise due to harmonics.

The invention will be described in further detail now by referring to examples.

EXAMPLE 1

A tubular green body for the tubular solid electrolyte 1 as shown in FIG. 6 with an outside diameter of 5 mm and an inside diameter of 3 mm was prepared by using a mixture consisting of 100 parts by weight of powder material containing 92 mole % of zirconia ($ZrO_2$) and 8 mole % of yttria ($Y_2O_3$), and 15 parts by weight of binder including 10 parts by weight of polyvinyl butyral and 5 parts by weight of dioctyl phthalate. A spiral resistor 2 and terminals 3 were deposited on the outer surface of the tubular green body for the tubular solid electrolyte 1 by applying a pasty mixture containing 90 parts by weight of iridium powder and 10 parts by weight of zirconia powder. A gastight layer 6 having the same chemical composition as that of the above-mentioned tubular green body was formed on the outer surfaces of the resistor 2 and the terminals 3. The thus prepared assembly was sintered at 1,700° C. in air. Whereby, a heater with solid electrolyte according to the present invention was produced.

The resistance of the heater with solid electrolyte thus produced was 3 ohms across the terminals 3. The heater was heated by applying an alternating current thereto through an inductor 10 from an AC power source 4 producing a 100 kHz output voltage of 50 V with a rectangular waveform. Consequently, the temperature of the central portion of the heater reached 1,600° C. in five minutes after starting the application of the alternating current. No deterioration was noticed at all after continuously using the heater under the above-mentioned conditions for 500 hours.

EXAMPLE 2

Figure 5:
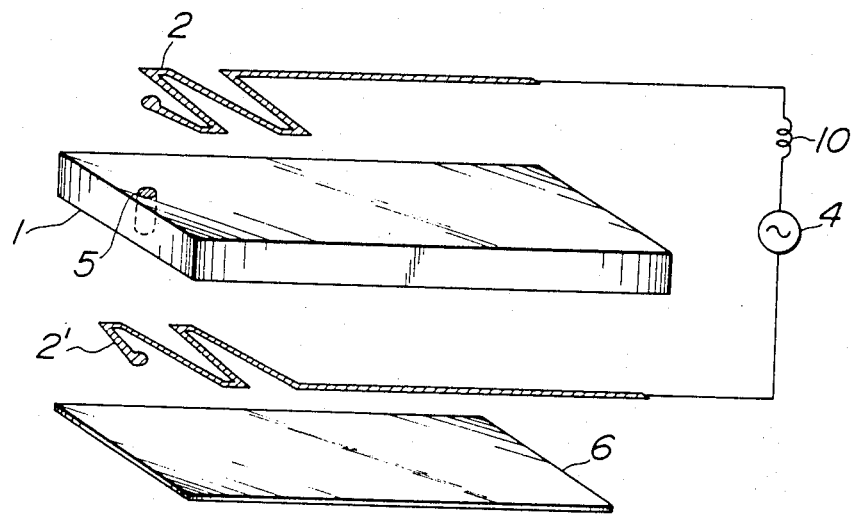
FIG. 5 is an exploded perspective view showing the mechanical construction and electric connection of another embodiment of the present invention.

A 1 mm thick planar zirconia green body was prepared by using a mixture consisting of 100 parts by weight of powder material containing 85 mole % of zirconia ($ZrO_2$) and 15 mole % of calcium oxide (CaO), 0.5 part by weight of clay as a sintering aid, and 13 parts by weight of binder including 8 parts by weight of methyl polyacrylate and 5 parts by weight of dioctyl phthalate. Resistors 2 and 2' as shown in FIG. 5 were formed on opposite surfaces of the thus prepared planar green body by the screen printing method while using a paste containing 85 parts by weight of alloy powder and 15 parts by weight of zirconia powder which alloy powder contained 80% of platinum and 20% of rhodium. The resistors 2 and 2' on the opposite surfaces of the planar zirconia green body were electrically connected by the same paste through a throughhole 5.

The surface of the zirconia green body carrying the one resistor 2' was covered by a gastight layer 6 having the same chemical composition as that of the above-mentioned zirconia green body. The assembly thus prepared was sintered at 1,600° C., so as to produce a heater with solid electrolyte according to the present invention.

The resistors 2 and 2' of the thus produced heater were heated by applying an alternating current thereto through an inductor 10 from an AC power source 4 producing a 10 kHz output voltage of 10 V with a sinusoidal waveform. The temperature of the two resistors 2 and 2' reached 1,450° C. in three minutes after starting the application of the alternating current. No deterioration was noticed at all after keeping the electric current through the serial resistors at this high temperature for 200 hours.

EXAMPLE 3

A 1 mm thick planar green body was prepared by using a mixture consisting of 100 parts by weight of powder of a proton-conductive solid electrolyte having a chemical composition of $SrCe_{0.95}Yb_{0.05}O_{3-\alpha}$, and 18 parts by weight of binder including 12 parts by weight of polyvinyl butyral and 6 parts by weight of dioctyl phthalate. As shown in FIG. 7, a resistor 2 and terminals 3 were formed on one side surface of the thus prepared planar green body by printing a paste containing 90 parts by weight of tungsten powder and 10 parts by weight of the same powder material as that of the above-mentioned solid electrolyte green body, and another 1 mm thick layer of the same chemical composition as that of the above-mentioned planar green body was overlaid on the surface carrying the thus formed resistor 2 and the terminals 3. The green bodies thus overlaid one above the other were sintered at 1,600° C. in hydrogen atmosphere, and then an auxiliary electrode 7 made of platinum was plated on one side surface of the thus sintered good. Whereby, a heater with solid electrolyte according to the present invention was produced. An AC power source 4 producing a 1 kHz output voltage of 5 V with a rectangular waveform was connected across the terminals 3 so as to heat the resistor 2, and simultaneously the output from the AC power source 4 was also rectified by a diode 8 and the rectified voltage was applied to the auxiliary electrode 7 through another resistor 9 so as to cause the resistor 2 to act as a cathode. As a result, the resistor 2 was heated to 1,000° C. No deterioration was noticed after keeping the electric current through the heater with solid electrode under the thus heated conditions for 200 hours.

As described in detail in the foregoing, the heater with solid electrolyte according to the present invention is simple in construction and yet it can be used in a very stable fashion up to a very high temperature, so that an excellent heater with solid electrolyte having a very high durability is provided. The heater with solid electrolyte of the invention can be used in various industrial fields; for instance, it can be used as the heater of a high-temperature furnace for general purposes, the heater of a firing device, the heater of any of various sensors using solid electrolyte, or the like. Accordingly, the heater with solid electrolyte of the invention is very useful in various industries.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. A method of heating a solid electrolyte which is ion-conductive at temperatures above room temperature, comprising:
    providing an electric resistance heating element in contacting engagement with a solid electrolyte wherein heat generated by said electric resistance heating element causes a temperature of the solid electrolyte to rise above room temperature, thereby reducing an electrical resistance of said electrolyte and permitting said electrolyte to become ion-conductive; and applying an alternating current from an AC power source connected to opposite ends of the electric resistance heating element so as to flow an alternating current to the electric resistance heating element, wherein said alternating current from the AC power source has a frequency of about 1 kHz to about 100 kHz such that an interface impedance between said solid electrolyte and said electric resistance heating element to which said AC source is connected is largely independent of an interface capacitance between said solid electrolyte and said electric resistance heating element, whereby heat is generated in the electric resistance heating element by flowing the alternating current therethrough and heat is also generated in the solid electrolyte by flowing an alternating current directly through the solid electrolyte, a heating of the solid electrolyte being dependent upon a temperature-sensitive resistance of the solid electrolyte being heated by the electric resistance heating element.

2. The method of claim 1, wherein said electric resistance heating element is embedded in the solid electrolyte.

3. The method of claim 2, wherein with solid electrolyte is oxygen-ion-conductive.

4. The method of claim 1, wherein said electric resistance heating element is tightly secured to at least one side surface of said solid electrolyte.

5. The method of claim 3, wherein said solid electrolyte is oxygen-ion-conductive.

6. The method of claim 1, wherein said solid electrolyte is oxygen-ion-conductive.

* * * * *